United States Patent [19]

Raddatz et al.

[11] Patent Number: 5,045,547
[45] Date of Patent: Sep. 3, 1991

[54] LEUKOTRIENE-INHIBITING SUBSTITUTED (QUINOLIN-2-YL-METHOXY)PHENYL-N,N'-SULPHONYLUREAS AND USE THEREAS

[75] Inventors: Siegfried Raddatz, Cologne; Klaus Mohrs, Wuppertal; Romanis Fruchtmann, Cologne; Christian Kohlsdorfer, Erftstadt; Reiner Müller-Peddinghaus; Pia Theisen-Popp, both of Bergisch Gladbach, all of Fed. Rep. of Germany

[73] Assignee: Bayer Aktiengesellschaft, Leverkusen, Fed. Rep. of Germany

[21] Appl. No.: 484,726

[22] Filed: Feb. 23, 1990

[30] Foreign Application Priority Data

Mar. 14, 1989 [DE] Fed. Rep. of Germany ....... 3908298

[51] Int. Cl.$^5$ ................. C07D 215/14; C07D 215/16; C07D 401/02; A61K 31/47
[52] U.S. Cl. .................................... 514/311; 546/171; 546/172; 544/331; 514/256; 514/312; 514/313; 514/317
[58] Field of Search ................. 546/172, 171; 514/311, 514/256, 312, 313, 314

[56] References Cited

U.S. PATENT DOCUMENTS 4,876,396 10/1989 Musser et al. ...................... 546/176

FOREIGN PATENT DOCUMENTS 0110405 6/1985 European Pat. Off. .

OTHER PUBLICATIONS

W. Forth, "Allgemein und spezielle Pharmakologie und Toxikologie", 4th edition, 1983, pp. 340–341.
J57/64675, "Substd. phenylurea derivs.–use as selective herbicides . . . ", JP 8,264,675, Agr. Chem. pp. 6-7 80/140091.

Primary Examiner—David B. Springer
Attorney, Agent, or Firm—Sprung Horn Kramer & Woods

[57] ABSTRACT

Lipoxygenase-inhibiting and leukotriene-inhibiting substituted (quinolin-2-yl-methoxy)phenyl-N,N'-sulphonylureas of the formula

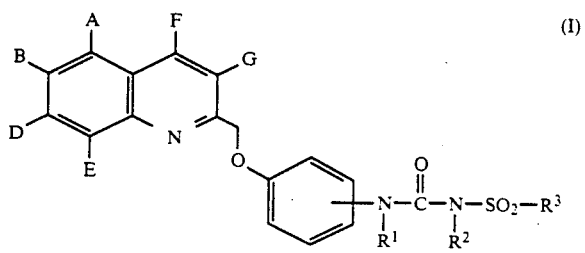

and physiologically acceptable salts thereof.

15 Claims, No Drawings

LEUKOTRIENE-INHIBITING SUBSTITUTED (QUINOLIN-2-YL-METHOXY)PHENYL-N,N'-SULPHONYLUREAS AND USE THEREAS

The invention relates to substituted (quinolin-2-yl-methoxy)phenyl-N,N,-sulphonylureas, to processes for their preparation and to their use in medicaments.

It is known that sulphonylureas have an antidiabetic action (cf. W. Forth, Allgemeine und Spezielle Pharmakologie und Toxikologie (General and Specific Pharmacology and Toxicology), 4th edition, 1983, B.I. Wissenschaftsverlag). In addition, N,N-dimethyl-N,-[3-(2-quinolyl-methoxy)phenyl-ureas have been described in JP 8,264,675, Appl. 80/140 091.

It is additionally known that substituted (quinolin-2-yl-methoxy)-phenyl derivatives show a lipoxygenase-inhibiting action (EP 110,405).

Substituted (quinolin-2-yl-methoxy)-N,N'-sulphonylureas of the general formula (I)

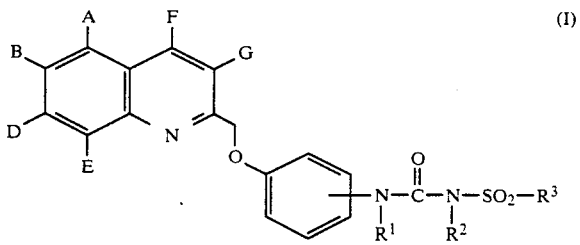

in which

A, B, D, E, F and G are identical or different and
represent hydrogen, hydroxyl, halogen, carboxyl, nitro, trifluoromethyl, trifluoromethoxy or a group of the formula —NR$^4$R$^5$, in which R$^4$ and R$^5$ are identical or different and denote hydrogen, straight-chain or branched alkyl having up to 8 carbon atoms or aryl having 6 to 10 carbon atoms,
represent straight-chain or branched alkyl, alkoxy or alkoxycarbonyl in each case having up to 12 carbon atoms, each of which is optionally substituted by hydroxyl, halogen, nitro, cyano or a group of the formula —NR$^4$R$^5$, in which R$^4$ and R$^5$ have the abovementioned meaning,
represent aryl having 6 to 10 carbon atoms, which is optionally substituted by halogen, hydroxyl, nitro, cyano, straight-chain or branched alkyl, alkoxy or alkoxycarbonyl in each case having up to 8 carbon atoms or by a group of the formula —NR$^4$R$^5$, in which R$^4$ and R$^5$ have the abovementioned meaning, R$^1$ and R$^2$ are identical or different and
represent hydrogen, or
cycloalkyl having 3 to 8 carbon atoms,
represent straight-chain or branched alkyl having up to 12 carbon atoms, which is optionally substituted by halogen, nitro, cyano, hydroxyl, trifluoromethyl, phenyl, cycloalkyl having 3 to 8 carbon atoms or by a group of the formula —NR$^4$R$^5$, in which R$^4$ and R$^5$ have the abovementioned meaning, R$^3$ has the abovementioned meaning of R$^1$ and R$^2$ and is identical or different to this, or
represents a 5- to 7-membered heterocycle having up to 4 different heteroatoms from the series comprising sulphur, oxygen or nitrogen, or aryl having 6 to 10 carbon atoms, the heterocycle and the aryl radical optionally being monosubstituted to trisubstituted by identical or different substituents from the series comprising halogen, nitro, cyano, hydroxyl, straight-chain or branched alkyl, alkylthio or alkoxy having up to 8 carbon atoms, trifluoromethyl, trifluoromethoxy or a group of the formula —NR$^4$R$^5$, where R$^4$ and R$^5$ have the abovementioned meaning, and their salts have now been found.

Within the framework of the present invention, physiologically acceptable salts are preferred. Physiologically acceptable salts of the substituted (quinolin-2-yl-methoxy)phenyl-N,N'-sulphonylureas can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts within the framework of the present invention are also salts of the monovalent metals, such as alkali metals, and the ammonium salts. Sodium salts, potassium salts and ammonium salts are preferred.

The compounds of the general formula (I) according to the invention surprisingly show a high in vitro activity as leukotriene inhibitors and a strong in vivo activity after oral administration.

Preferred compounds of the general formula (I) are those in which

A, B, D, E, F and G are identical or different and
represent hydrogen, hydroxyl, fluorine, chlorine, bromine, carboxyl, nitro, trifluoromethyl, trifluoromethoxy or a group of the formula —NR$^4$R$^5$, in which R$^4$ and R$^5$ are identical or different and denote hydrogen, straight-chain or branched alkyl having up to 6 carbon atoms or phenyl,
represent straight-chain or branched alkyl, alkoxy or alkoxycarbonyl in each case having up to 10 carbon atoms, each of which is optionally substituted by hydroxyl, fluorine, chlorine, bromine, nitro, cyano or a group of the formula —NR$^4$R$^5$, in which R$^4$ and R$^5$ have the abovementioned meaning,
represent phenyl which is optionally substituted by fluorine, chlorine, bromine, hydroxyl, nitro, cyano, straight-chain or branched alkyl, alkoxy or alkoxycarbonyl in each case having up to 6 carbon atoms or by a group of the formula —NR$^4$R$^5$ in which R$^4$ and R$^5$ have the abovementioned meaning, R$^1$ and R$^2$ are identical or different and
represent hydrogen or
cyclopropyl, cyclobutyl, cyclopentyl, cyclohexyl or cycloheptyl,
represent straight-chain or branched alkyl having up to 8 carbon atoms, which is optionally substituted by fluorine, chlorine, bromine, nitro, cyano, hydroxyl, trifluoromethyl, phenyl, cyclopropyl, cyclobutyl, cyclopentyl, cyclohexyl, cycloheptyl or by a group of the formula —NR$^4$R$^5$, in which R$^4$ and R$^5$ have the abovementioned meaning, $R^3$ has the abovementioned meaning of $R^1$ and $R^2$ and is identical or different to this, or represents thienyl, furanyl, pyrryl, pyrimidyl, pyridyl or phenyl, which are optionally mono-substituted or disubstituted by identical or different substituents from the series comprising fluorine, chlorine, bromine, nitro, cyano, hydroxyl, straight-chain or branched alkyl, alkylthio or alkoxy having up to 6 carbon atoms, trifluoromethyl, trifluoromethoxy or by a group of the formula $-NR^4R^5$ and their salts.

Particularly preferred compounds of the general formula (I) are those in which

A, B, D, E, F and G are identical or different and represent hydrogen, fluorine, chlorine, bromine, nitro or trifluoromethyl represent methyl, ethyl, propyl, isopropyl, butyl or tert.butyl, $R^1$ and $R^2$ are identical or different and represent hydrogen or represent cyclopropyl, cyclopentyl or cyclohexyl, represent straight-chain or branched alkyl having up to 6 carbon atoms, which is optionally substituted by fluorine, chlorine, bromine, phenyl, cyclopentyl, cyclohexyl or cycloheptyl, $R^3$ has the abovementioned meaning of $R^1$ and $R^2$ and is identical or different to this, or represents phenyl which is optionally substituted by fluorine, chlorine, bromine or straight-chain or branched alkyl having up to 4 carbon atoms, and their salts.

Very particularly preferred compounds of the general formula (I) are those in which the quinolylmethoxy grouping on the phenyl is in the 4-position to the sulphonylurea group.

Very particularly preferred compounds of the general formula (I) selected are those in which A, B, D, E, F and G represent hydrogen, $R^2$ and $R^3$ have the abovementioned meaning and $R^1$ represents cyclopentyl or methylcyclohexyl, and in which A, B, D, E, F, G and $R^2$ have the abovementioned meaning, $R^1$ represents hydrogen, n-pentyl or cyclopentyl and $R^3$ represents benzyl, and their salts.

In addition, processes for the preparation of the compounds of the general formula (I) according to the invention

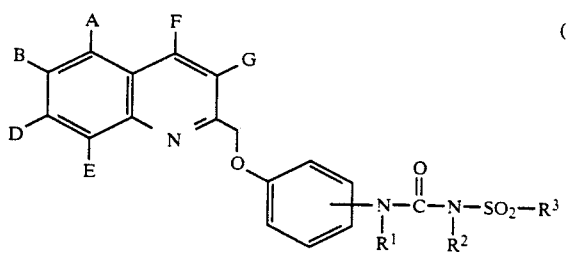

in which A, B, D, E, F, G, $R^1$, $R^2$ and $R^3$ have the abovementioned meaning, have been found, which are characterized in that

[A] compounds of the general formula (II),

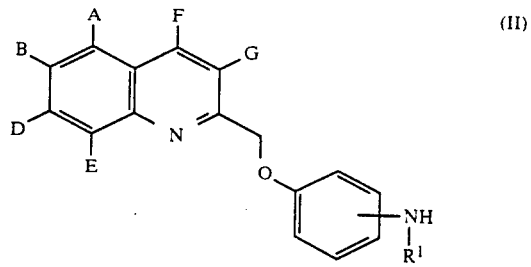

in which A, B, D, E, F, G and $R^1$ have the abovementioned meaning, are reacted with sulphonyl isocyanates of the general formula (III)

in which $R^3$ has the abovementioned meaning, in an inert solvent to give compounds of the general formula (Ia)

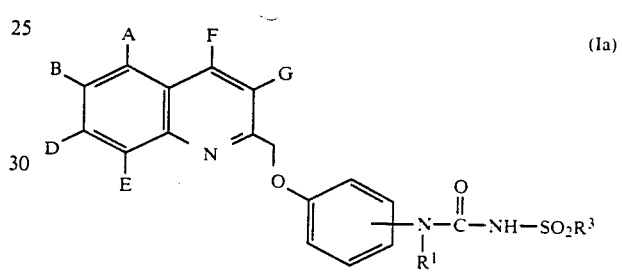

in which A, B, D, E, F, G, $R^1$ and $R^2$ have the abovementioned meaning, and in the case of the compounds of the formula (I) with $R^2 \neq H$, the compounds of the formula (Ia) are subsequently alkylated in inert solvents with alkylating agents, or in that

[B] compounds of the general formula (IV)

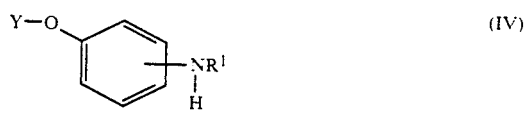

in which $R^1$ has the abovementioned meaning and

Y—represents a typical hydroxyl protective group such as, for example, benzyl or tert.butyl, are first reacted with compounds of the general formula (III) in inert solvents to give compounds of the general formula (V)

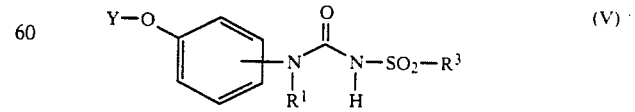

in which $R^1$, $R^3$ and Y have the abovementioned meaning, then the protective group Y is removed by a customary method, and are subsequently esterified with halogenomethylquinolines of the formula (VI)

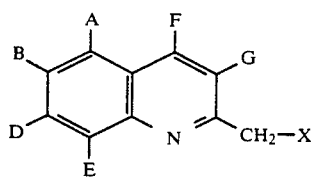
(VI)

in which
A, B, D, E, F and G have the abovementioned meaning and
X—represents halogen,
and in the case of the compounds of the formula (I), with $R^2 \sim H$, are subsequently alkylated in inert solvents with alkylating agents, or in that
[C] compounds of the general formula (VII)

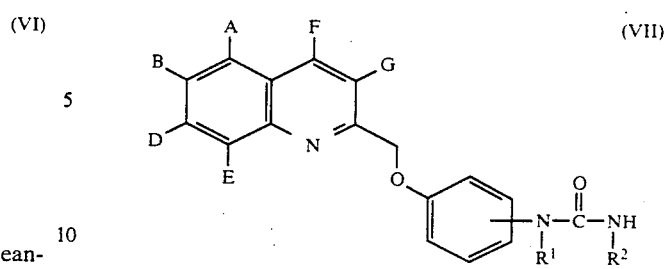
(VII)

in which A, B, D, E, F, G, $R^1$ and $R^2$ have the abovementioned meaning, are reacted with sulphonyl halides of the general formula (VIII)

$$R^3-SO_2-X \qquad (VIII)$$

in which $R^3$ and X have the abovementioned meaning, in inert solvents, if appropriate in the presence of bases.

The process according to the invention can be illustrated by the following equations:

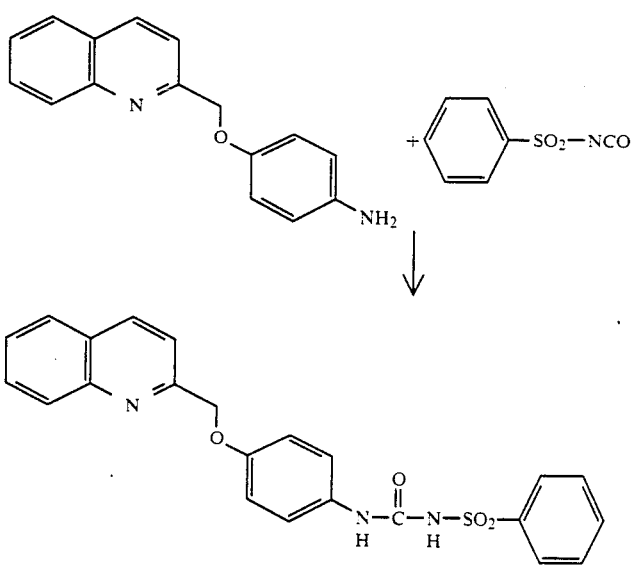
[A]

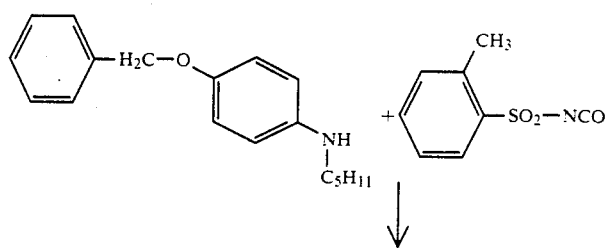
[B]

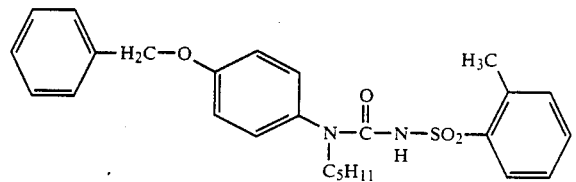

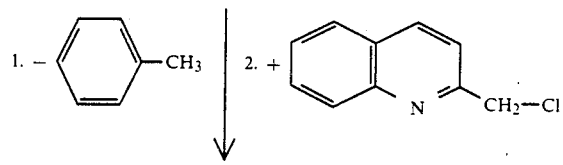

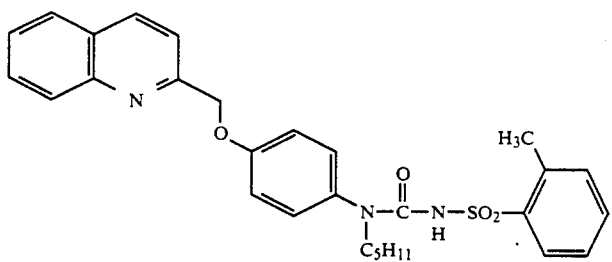

[C]

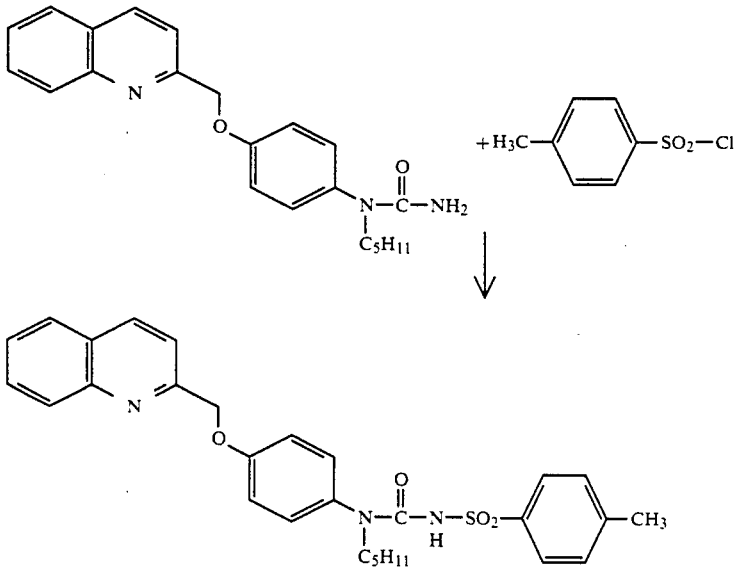

Suitable solvents for process [A] according to the invention are customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or mineral oil fractions, or halogenated hydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethyl phosphoramide, acetonitrile, acetone or nitromethane. It is also possible to use mixtures of the solvents mentioned. Dichloromethane is preferred.

Process [A] according to the invention is in general carried out in a temperature range from −80° C. to +80° C., preferably from −80° C. to 0° C.

Process [A] according to the invention is in general carried out at normal pressure. However, it is also possible to carry out the process at elevated pressure or at reduced pressure (for example in a range from 0.5 to 5 bar).

In general, 1 to 3 moles, preferably 1 to 2 moles, particularly preferably 1 mole of sulphonyl isocyanate, are employed per mole of thiamine.

The sulphonyl isocyanates of the general formula (III) are known or can be prepared by known methods [C. King, J. Org. Chem. 25, 352 (1960); F. Effenberger, R. Gleiter, Chem. Ber. 97, 1576 (1964); H. Ulrich, A.A.R. Sayigh, Angew. Chem. 78, 761 (1966); Houben-Weyl VIII, 128].

The compounds of the general formula (II) are known per se or can be prepared by customary methods (cf. Ger. Offen. DE 3,607,382).

The solvents mentioned for process [A] can be used as solvents for all steps of process [B].

The conditions mentioned under process [A] apply to the reaction with sulphonyl isocyanates.

The removal of the protective groups from the corresponding ethers is carried out by customary methods, for example by hydrogenolytic cleavage of the benzyl ethers in the abovementioned inert solvents using hydrogen gas in the presence of a catalyst [cf. in addition Th. Greene: "Protective Groups in Organic Synthesis", J. Wiley & Sons, 1981, New York].

The etherification can be carried out in inert organic solvents, if appropriate in the presence of a base.

Solvents for the etherification can be inert organic solvents which do not change under the reaction conditions. These preferably include ethers such as, for example, dioxane, tetrahydrofuran or diethyl ether, halogenated hydrocarbons such as dichloromethane, trichloromethane, tetrachloromethane, 1,2-dichloroethane or trichloroethylene, hydrocarbons such as benzene, xylene, toluene, hexane or cyclohexane, or mineral oil fractions, nitromethane, dimethylformamide, acetonitrile, acetone or hexamethylphosphoramide. It is also possible to employ mixtures of these solvents.

Inorganic or organic bases can be employed as bases for the etherification. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate, or organic amines (trialkyl($C_1$-$C_6$) amines) such as triethylamine, or heterocycles such as pyridine, methylpiperidine, piperidine or morpholine.

It is also possible to employ alkali metals, such as sodium, and their hydrides, such as sodium hydride, as bases.

The etherification is in general carried out in a temperature range from 0° C. to +150° C., preferably from +10° C. to +100° C.

The etherification, like all other steps of process [B] according to the invention, is in general carried out at normal pressure. However, it is also possible to carry out the process at reduced pressure or elevated pressure (for example in a range from 0.5 to 5 bar).

In general, 0.5 to 5, preferably 1 to 2 moles of halide, are employed relative to one mole of the reaction component. The base is in general employed in an amount from 0.5 to 5 moles, preferably from to 3 moles relative to the halide.

The compounds of the general formula (IV) and (V) are known per se or can be prepared by customary methods [cf. A. Ulrich, B. Tucker, A.A.R. Sayigh, J. Org. Chem. 31. 2658 (1966).

The compounds of the general formula (VI) and their preparation are likewise known.

For example, the following halides can be used according to the invention:
8-chloro-2-chloromethyl-quinoline
7-chloro-2-chloromethyl-quinoline
6-fluoro-2-chloromethyl-quinoline The solvents mentioned under process [A] can be used as solvents for process [C].

Bases for process [C] according to the invention can be customary basic compounds. These preferably include alkali metal or alkaline earth metal hydroxides such as lithium hydroxide, sodium hydroxide, potassium hydroxide or barium hydroxide, or alkali metal hydrides, such as sodium hydride, or alkali metal or alkaline earth metal carbonates such as sodium carbonate, sodium hydrogen carbonate, potassium carbonate or calcium carbonate, or alkali metal alkoxides such as, for example sodium methoxide, sodium ethoxide, potassium methoxide, potassium ethoxide or potassium tert.-butoxide, or alkali metal amides such as sodium amide or lithium diisopropylamide, or organic amines such as benzyltrimethylammonium hydroxide, tetrabutylammonium hydroxide, pyridine, dimethylamino pyridine, triethylamine, N-methylpiperidine, 1,5-diazobicyclo-[4.3.0] non-5-ene or 1,5-diazobicyclo[5.4.0]undec-5-ene.

Process [C] according to the invention is in general carried out in a temperature range from −30° C. to +150° C., preferably from −20° C. to +80° C.

Process [C] according to the invention is in general carried out at normal pressure. However, it is also possible to carry out the process at elevated pressure or at reduced pressure (for example in a range from 0.5 to 5 bar).

In general, 1 to 5 moles, preferably 1 to 2 moles, particularly preferably 1 mole of sulphonyl halide, are employed relative to 1 mole of the amine. The base is in general employed in an amount of 1 to 10 moles, preferably of 1 to 5 moles, relative to the sulphonyl halide.

The compounds of the general formula (VII) are known per se or can be prepared by customary methods [cf. JP 8,264,675; Appl. 80/140.091].

The sulphonyl halides of the general formula (VIII) are known [cf. R.V. Vitzgert, Uspekhi, Khimii 32, 3 (1963); Russian Chem. Rev. 32, 1 (1963)].

Examples of sulphonyl halides which may be mentioned for process [C] according to the invention are:
4-phenyl-sulphonyl chloride
4-toluene-sulphonyl chloride
4-chlorophenyl-sulphonyl chloride
4-methoxyphenyl-sulphonyl chloride
propyl-sulphonyl chloride
butyl-sulphonyl chloride
isobutyl-sulphonyl chloride Alkylating agents which can be employed in processes [A] and [B] are, for example, ($C_1$–$C_8$)-alkyl halides, sulphonic acid esters or substituted or unsubstituted ($C_1$–$C_6$)-dialkyl or ($C_6$–$C_{10}$)-diaryl sulphates, preferably methyl iodide, p-toluenesulphonic acid esters or dimethyl sulphate.

The alkylation is carried out in the abovementioned solvents at temperatures from 0° C. to +150° C., preferably at room temperature to +100° C. at normal pressure.

The substituted 3- or 4-(quinolin-2-yl-methoxy)phenyl-N,N′-sulphonylureas according to the invention can be employed as active substances in medicaments. The substances can act as inhibitors of enzymatic reactions in the context of arachidonic acid metabolism, in particular of lipoxygenase.

They are thus preferred for the treatment and prevention of disorders of the airways such as allergies-/asthma, bronchitis, emphysema, shock lung, pulmonary hypertension, inflammations/rheumatism and oedemas, thromboses and thromboembolisms, ischaemias (peripheral, cardiac and cerebral circulatory disturbances), cardiac and cerebral infarcts, cardiac arrhythmias, angina pectoris, arteriosclerosis, in tissue transplants, dermatoses such as psoriasis, inflammatory dermatoses, for example eczema, dermatophyte infections, infections of the skin by bacteria, metastases and for cytoprotection in the gastrointestinal tract.

The substituted (quinolyl-2-yl-methoxy)phenyl-N,N′-sulphonylureas according to the invention can be used both in human medicine and in veterinary medicine.

The pharmacological activity data of the substances according to the invention are determined by the following method:

As a measure of the lipoxygenase inhibition, the release of leukotriene $B_4$ (LTB.) from polymorphonuclear rat leucocytes (PMN) was determined after addition of substances and Ca ionophore by means of reverse phase HPLC according to Borgeat, P. et al., Proc. Nat. Acad. Sci. 76, 2148–2152 (1979). The in vivo activity of the compounds was detected using the mouse ear inflammation model according to Young, J. M. et al., J. of Investigative Dermatology 82, 367–371, (1984).

In Table 1, the values obtained by this test, for example, are shown for some compounds according to the invention:

TABLE 1

| Example | LO inhibition $IC_{50}$ ($\mu M$) |
|---------|-----------------------------------|
| 3 | 0.036 |
| 4 | 0.033 |
| 5 | 0.41 |
| 6 | 0.36 |
| 7 | 0.24 |
| 8 | 0.29 |

Using inert non-toxic, pharmaceutically suitable excipients or solvents, the new active compounds can be converted in a manner known per se into the customary formulations, such as tablets, capsules, coated tablets, pills, granules, aerosols, syrups, emulsions, suspensions and solutions. In this connection, the therapeutically active compound should in each case be present in the preparation in a concentration of about 0.5 to 90% by weight, preferably from 10 to 70% by weight, i.e. in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, if appropriate organic solvents can be used as auxiliary solvents.

Examples of auxiliaries which may be mentioned are: water, non-toxic organic solvents such as paraffins (for examples mineral oil fractions), vegetable oils (for example ground nut/sesame oil), alcohols (for example ethyl alcohol, glycerol), glycols (for example propylene glycol, polyethylene glycol, polyethylene glycol), solid excipients, such as ground natural minerals, for example kaolins, clays, talc, chalk), ground synthetic minerals (for example highly disperse silica, silicates), sugars, (for example sucrose, lactose and dextrose), emulsifiers, (for example polyoxyethylene fatty acid esters, polyoxyethylene fatty alcohol ethers, alkyl sulphonates and aryl sulphonates), dispersants (for example lignin-sulphite waste liquors, methyl cellulose, starch and polyvinylpyrrolidone) and lubricants (for example magnesium stearates, talc, stearic acid and sodium lauryl sulphate).

Administration can be carried out in a customary manner, preferably orally or parenterally, in particular perlingually or intravenously. In the case of oral administration, tablets can of course also contain additions such as sodium citrates, calcium carbonates and dicalcium phosphates together with various additives, such as starch, preferably potato starch, gelatin and the like in addition to the excipients mentioned. Furthermore, lubricants, such as magnesium stearate, sodium lauryl sulphate and talc can additionally be used for tableting. In the case of aqueous suspensions and/or elixirs, which are intended for oral administration, various flavor-improvers or colorants can be added to the active compounds in addition to the abovementioned auxiliaries.

For the case of parenteral administration, solutions of the active compounds can be employed using suitable liquid excipients In general, it has proved advantageous on intravenous administration to administer amounts of about 0.01 to 10 mg/kg, preferably about 0.01 to 5 mg/kg of bodyweight, to attain effective results. On oral administration, the dosage is in general about 0 1 to 200 mg/kg, preferably 1 to 100 mg/kg of bodyweight.

In spite of this it may be necessary to deviate from the amounts mentioned, depending on the bodyweight or the type of application route, on individual behavior towards the medicament, the manner of its formulation and the point in time or interval at which administration takes place. Thus, in some cases it may be sufficient to manage with less than the minimum amount previously mentioned, while in other cases the upper limit mentioned must be exceeded. In the case of the administration of relatively large amounts, it may be advisable to divide these into a number of individual doses over the day.

PREPARATION EXAMPLES

EXAMPLE 1

2-(4-Aminophenoxymethyl)quinoline

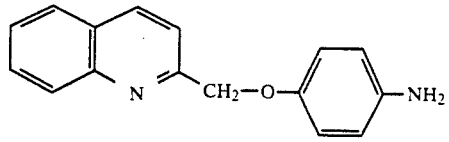

117.8 g (0.42 mol) of 2-(4-nitrophenoxymethyl)quinoline were dissolved in 1 l of methanol/tetrahydrofuran (1:1). About 5 g of Raney nickel were then added and the mixture was warmed to 35° C. 63.1 g (1.26 mol) of hydrazine hydrate $\times H_2O$ were then added dropwise and the mixture was stirred overnight. The residue was filtered off, the solution was concentrated in vacuo and the residue was taken up with methylene chloride. The mixture was then washed with water and conc. hydrochloric acid was added to the organic phase. The precipitate deposited was filtered off, washed with 2 N hydrochloric acid, dissolved in water and rendered alkaline with 20% strength NaOH. The residue was dried in vacuo.

Yield: 88.0 g (92.1% of theory)

M.p. =131° C.

EXAMPLE 2

2-(4-n-Pentylaminophenoxymethyl)quinoline

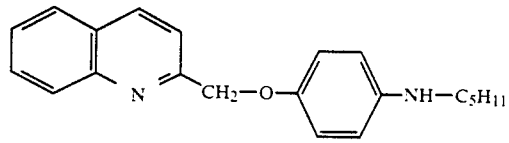

12.5 g (0.05 mol) of the compound from Example 1 were dissolved in methanol. 2.0 g (0.03 mol) of sodium cyanoborohydride were then added in portions. 5.3 ml (0.05 mol) of pentanal were cautiously added dropwise to the solution. After stirring for 48 h at room temperature, the solution was concentrated in vacuo, the residue was dissolved in methylene chloride and the solution was washed with 2N hydrochloric acid. The organic phase was separated off, dried and concentrated in vacuo, and the residue was put through a 1000 cm³ silica gel 60 column. The system methylene chloride/ethyl acetate 7:3 was employed as the eluent.

Yield: 5.5 g (34.4% of theory)

M.p. =54°-55° C.

EXAMPLE 3

N-(4-methylphenylsulphonyl)-N'-pentyl-N'-4-(2-quinolyl-methoxy)phenylurea.

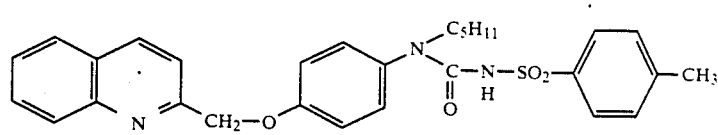

1.9 g (0.006 mol) of the compound from Example 2 were dissolved in 50 ml of methylene chloride and the solution was cooled to −78° C. The apparatus was then flushed several times with argon. 1.18 g (0.006 mol) of p-tolylsulphonyl isocyanate were then added dropwise under argon. After stirring for 1 hour at −78° C., the mixture was warmed to room temperature and concentrated in vacuo. The oil was suspended with ether, first heated to room temperature and then cooled. The product crystallized out in the course of this, the residue was filtered off with suction and dried in vacuo.

Yield: 2.6 g (83.8% of theory)
M.p. = 157° C.

EXAMPLE 4

N-(2-methylphenylsulphonyl)-N'-pentyl-N'-4-(2-quinolylmethoxy)phenylurea

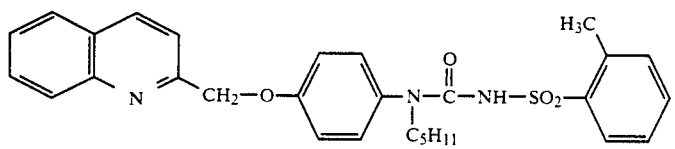

The reaction was carried out in analogy to the directions for Example 3 from 3.0 g (0.0094 mol) of the compound of Example 3 from 3.0 g (0.0094 mol) of the compound of Example 1 and 1.8 g (0.0094 mol) of o-tolylsulphonyl isocyanate Yield: 4.3 g (88.5% of theory)
M.p. = 174° C.

EXAMPLE 5

N-(2-methylphenylsulphonyl)-N'-4-(2-quinolymethoxy)phenylurea

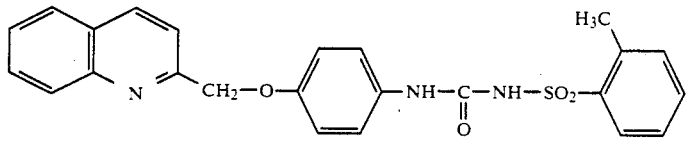

6.25 g (0.025 mol) of the compound from Example 1 and 5.1 g (0.025 mol) of o-tolylsulphonyl isocyanate were reacted in analogy to the directions for Example 3.

Yield: 11.0 g (98.4% of theory)
M.p. = 142° C.

EXAMPLE 6

N-(4-methylphenylsulphonyl)-N'-4-(2-quinolymethoxy)-phenylurea

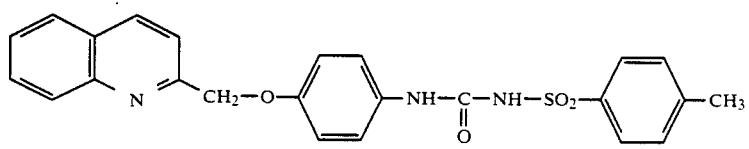

6.25 g (0.025 mol) of the compound from Example 1 were reacted with 4.9 g (0.025 mol) of p-tolylsulphonyl isocyanate in analogy to the directions for Example 3.

Yield: 11.1 g (99.3% of theory)
M.p. = 168° C.

The compounds shown in the following table can be prepared analogously to the directions for Examples 5 and 6:

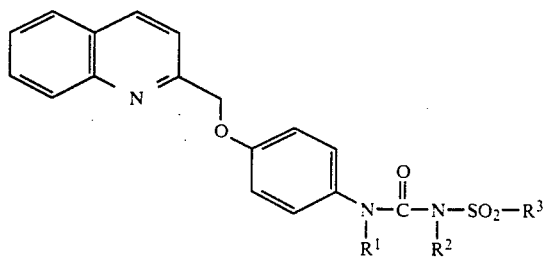

| Example No. | R¹ | R² | R³ | M.p.: |
|---|---|---|---|---|
| 7 | cyclopentyl | H | 4-CH₃-phenyl | 147° C. (dec.) |
| 8 | 1-methylcyclopentyl | H | 2-CH₃-phenyl | 178° C. (dec.) |

EXAMPLE 9

N-Methanesulphonyl-N'-4-(2-quinolinylmethoxy)-phenylurea

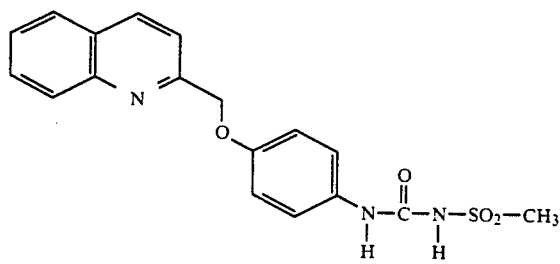

The title compound was prepared analogously to the directions for Example 3 from 2.5 g (0.01 mol) of the compound from Example 1 and 1.2 g (0.01 mol) of methanesulphonyl isocyanate.

Colorless crystals, m.p.: 187° C. (dec.)
Yield: 3.5 g (=94.3% of theory).

EXAMPLE 10

N-Benzylsulphonyl-N'-4-(2-quinolinylmethoxy)-phenylurea

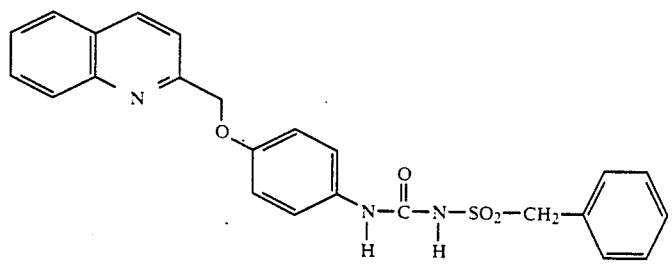

The title compound was prepared in analogy to Example 3 from 2.5 g (0.01 mol) of the compound from Example 1 and 2.0 g (0.01 mol) of benzylsulphonyl isocyanate.

Colorless crystals, m.p.: 183° C. (dec.)
Yield: 3.5 g (=78.2% of theory).

EXAMPLE 11

N-Mesyl-N'-n-pentyl-N'-4-(2-quinolinylmethoxy)-phenylurea

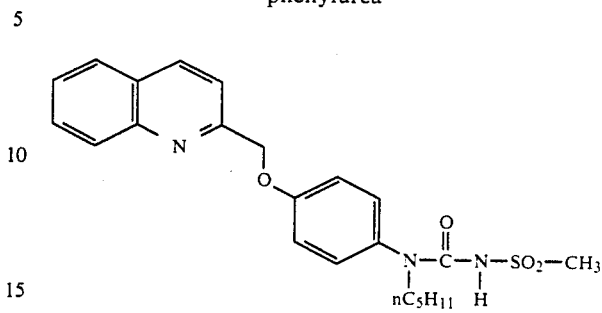

The title compound was prepared from 1.92 g (0.006 mol) of the compound from Example 2 and 0.73 g (0.006 mol) of methanesulphonyl isocyanate analogously to the directions for Example 3.

Colorless, glassy substance,
Yield: 1.4 g (52.9% of theory).

EXAMPLE 12

N-Benzylsulphonyl-N'-n-pentyl--N'-4-(2-quinolinylmethoxy)urea

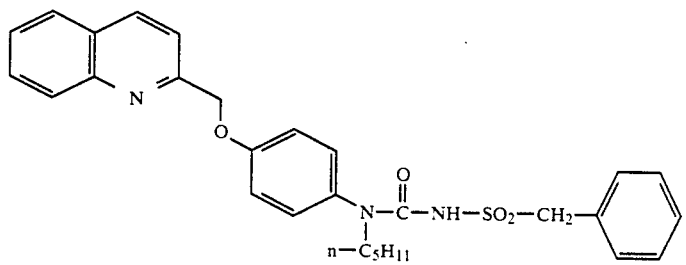

The title compound was prepared from 2.8 g (0.0088 mol) of the compound from Example 2 and 2.2 g (0.0088 mol) of benzylsulphonyl isocyanate analogously to the directions for Example 3.

Colorless, glassy substance,
Yield: 1.9 g (=41.7% of theory).

EXAMPLE 13

2-(4-Cyclohexyl-methyl-amino-phenoxymethyl)quinoline

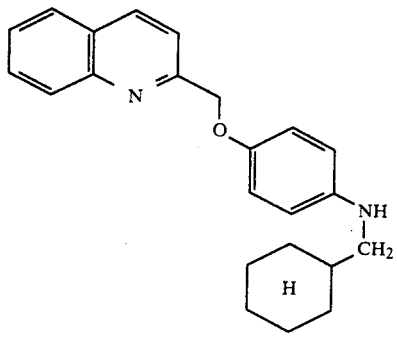

10 g (0.04 mol) of the compound from Example 1, 7.1 g (0.04 mol) of cyclohexyl-methyl bromide, 8.1 g (0.08 mol) of triethylamine and 5.6 g (0.04 mol) of potassium carbonate are stirred at 60°–70° C. overnight in 40 ml of dimethylformamide (dried) under an argon atmosphere. After cooling, the mixture is concentrated to dryness in vacuo and taken up in dichloromethane, and the solution is shaken twice with 1 N sodium hydroxide solution. After washing until neutral and drying with sodium sulphate, the solution is reduced to a small volume in vacuo and the residue is separated by column chromatography (silica gel 60, dichloromethane/ethylacetate =20/1). After concentrating the appropriate fraction, the slightly yellowish residue is crystallized from n-hexane Colorless crystals, m.p.: 94° C.,
Yield: 6.8 g (49.1% of theory).

EXAMPLE 14

N-Mesyl-N'-cyclohexyl-methyl-N'-4-(2-quinolinylmethoxy)phenylurea

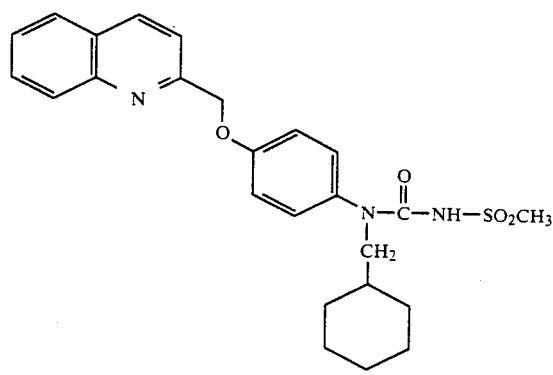

The title compound was prepared from 2.1 g (0.006 mol) of 2-(4-cyclohexylmethyl-aminophenoxymethyl)-quinoline (Example 13) and 0.73 g (0.006 mol) of methanesulphonyl isocyanate in analogy to the directions for Example 3.

Colorless crystals, m.p.: 171° C.,
Yield: 2.5 g (89.1% of theory).

EXAMPLE 15

2-(4-Cyclopentylaminophenoxymethyl)-quinoline

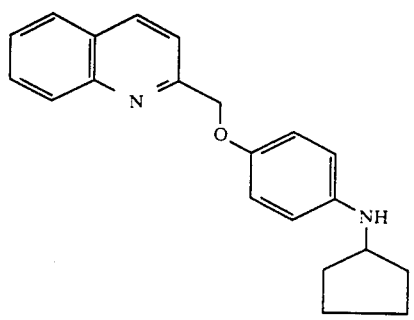

The title compound was prepared at a temperature of +40°–+50° C. from 10 g (0.04 mol) of the compound from Example 1 and 6 g (0.04 mol) of cyclopentyl bromide in analogy to Example 13.

Colorless crystals, m.p.: 88° C.,
L- Yield 0.6 g (51.9% of theory).

EXAMPLE 16

N-Mesyl-N'-cyclopentyl-N'-4-(2-quinolinylmethoxy)-phenylurea

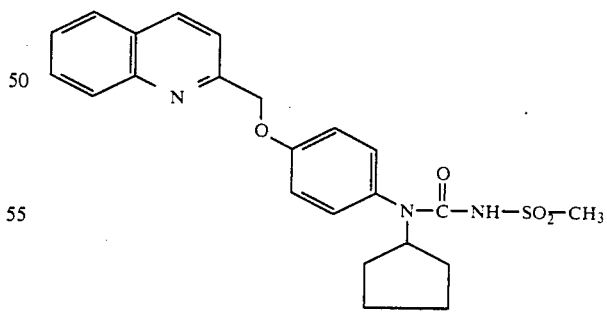

The title compound was prepared in analogy to Example 3 from 1.6 g (0.005 mol) of the compound from Example 15 and 0.6 g (0.005 mol) of methanesulphonyl isocyanate.

Colorless crystals, m.p.: 175° C. (dec.),
Yield 1.3 g (59.2% of theory).

EXAMPLE 17

N-Benzylsulphonyl-N'-cyclopentyl-N'-4-(2-quinolinylmethoxy)-phenylurea

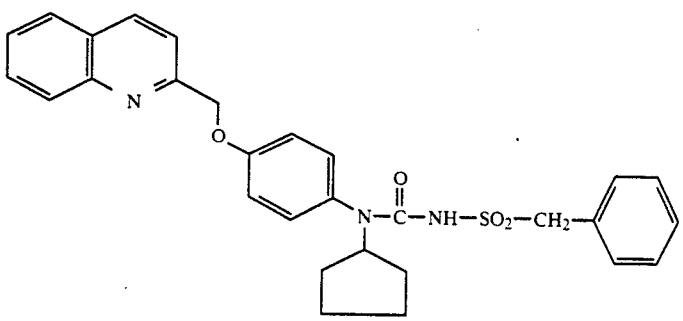

The title compound was prepared from 3.2 g (0.01 mol) of the compound from Example 5 and 2.0 g (0.01 mol) of benzylsulphonyl isocyanate in analogy to Example 3.

Colorless, glassy substance,
Yield: 1.1 g (21.3% of theory).

EXAMPLE 18

N-Benzylsulphonyl-N'-4-(2-quinolinylmethoxy)-phenylurea sodium salt

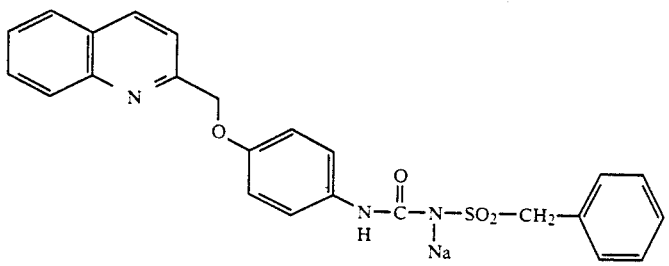

1 g of the compound from Example 10 (0.0022 mol) was dissolved in ethanol/tetrahydrofuran and the equimolar amount of 1 N sodium hydroxide solution was added. The solution was concentrated to dryness in vacuo and dried at a high temperature.

Colorless substance, m.p.: >229° C. (dec.)

EXAMPLE 19

2-(3-Aminophenoxymethyl)-quinoline

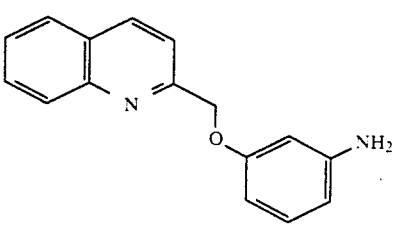

The compound was prepared from 50 g (0.178 mol) of 2-(.3-nitrophenoxymethyl)-quinoline analogously to the directions for Example 1. The recrystallization was carried out from diisopropyl ether.

Colorless crystals, m.p.: 100° C.,
Yield: 40.7 g (91.5% of theory).

EXAMPLE 20

N-Tosyl-N'-3-(2-quinolinylmethoxy)-phenylurea

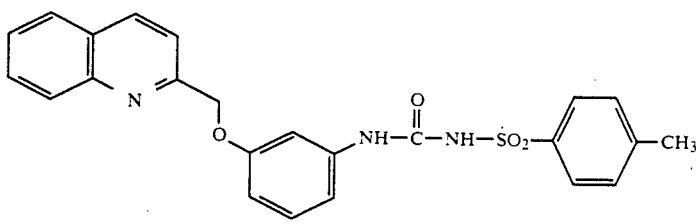

The title compound was prepared from 2 g (0.008 mol) of the compound from Example 19 and 1.58 g (0.008 mol) of 4-toluenesulphonyl isocyanate in analogy to the directions for Example 3.

Colorless crystals, m.p.: 121-122° C.,
Yield: 2.1 g (61.7% of theory).

EXAMPLE 21

N-o-Tosyl-N'-3-(2-quinolinylmethoxy)-phenylurea

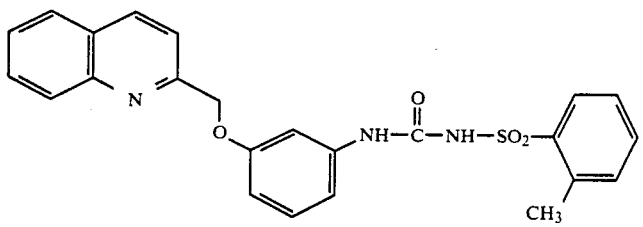

The title compound was prepared from 2 g (0.008 mol) of the compound from Example 19 and 1.58 g (0.008 mol) of 2-toluenesulphonyl isocyanate analogously to the directions for Example 3.

Colorless crystals, m.p.: 125° C.,

Yield: 2.1 g (61.7% of theory).

It will be understood that the specification and examples are illustrative but not limitative of the present invention and that other embodiments within the spirit and scope of the invention will suggest themselves to those skilled in the art.

What is claimed is:

1. A substituted (quinolin-2-yl)methoxy)phenyl-N,N'-sulphonylurea of the formula

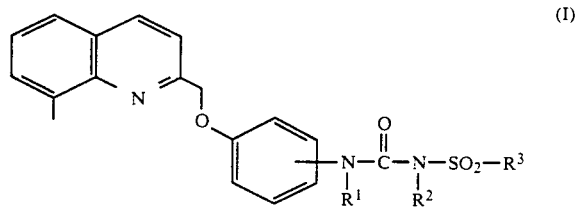

(I)

in which
  $R^1$ and $R^2$ are identical or different and
    represent hydrogen,
    cycloalkyl having 3 to 8 carbon atoms, or represent straight-chain or branched alkyl having up to 12 carbon atoms, which is optionally substituted by halogen, nitro, cyano, hydroxyl, trifluoromethyl, phenyl, cycloalkyl having 3 to 8 carbon atoms or by a group of the formula —$NR^4R^5$,
  $R^3$ has the above mentioned meaning of $R^1$ and $R^2$ is identical or different to this, or represents a heterocycle from the group consisting of thienyl, furonyl, pyrryl, pyrimidyl or pyridyl) having 6 to 10 carbon atoms, optionally being monosubstituted to trisubstituted by identical or different substituents from the group consisting of halogen, nitro, cyano, hydroxyl, straight-chain or branched alkyl, alkylthio or alkoxy having up to 8 carbon atoms, trifluoromethyl, trifluoromethoxy and a group of the formula —$NR^4R^5$, and
  $R^4$ and $R^5$ are identical or different and denote hydrogen, straight-chain or branched alkyl having up to 8 carbon atoms or aryl having 6 to 10 carbon atoms, or a physiologically acceptable salt thereof.

2. A substituted (quinolin-2-yl-methoxy)phenyl-N,N'-sulphonylurea or salt thereof according to claim 1, in which
  $R^1$ and $R^2$ are identical or different and
    represent hydrogen,
    cyclopropyl, cyclobutyl, cyclopentyl, cyclohexyl or cycloheptyl, or
    represent straight-chain or branched alkyl having up to 8 carbon atoms, which is optionally substituted by fluorine, chlorine, bromine, nitro, cyano, hydroxyl, trifluoromethyl, phenyl, cyclopropyl, cyclobutyl, cyclopentyl, cyclohexyl, cycloheptyl or by a group of the formula —$NR^4R^5$,
  $R^3$ has the abovementioned meaning of $R^1$ and $R^2$ and is identical or different to this, or represents thienyl, furanyl, pyrryl, pyrimidyl, pyridyl or phenyl, which are optionally mono-substituted or disubstituted by identical or different substituents from the group consisting of fluorine, chlorine, bromine, nitro, cyano, hydroxyl, straight-chain or branched alkyl, alklythio or alkoxy having up to 6 carbon atoms, trifluoromethyl, trifluoromethoxy or by a group of the formula —$NR^4R^5$, and
  $R^4$ and $R^5$ are identical or different and denote hydrogen, straight-chain or branched alkyl having up to 6 carbon atoms or phenyl.

3. A substituted (quinolin-2-yl-methoxy)phenyl-N,N'-sulphonylurea or salt thereof according to claim 1, in which
  $R^1$ and $R^2$ are identical or different and
    represent hydrogen,
    represent cyclopropyl, cyclopentyl or cyclohexyl, or
    represent straight-chain or branched alkyl having up to 6 carbon atoms, which is optionally substituted by fluorine, chlorine, bromine, cyclopentyl, cyclohexyl, cycloheptyl, or phenyl,
  $R^3$ has the abovementioned meaning of $R^1$ and $R^2$ and is identical or different to this, or represents phenyl which is optionally substituted by fluorine, chlorine, bromine or straight-chain or branched alkyl having up to 4 carbon atoms.

4. A substituted (quinolin-2-yl-methoxy)phenyl-N,N'-sulphonylurea or salt thereof according to claim 3, in which the quinolyl-methoxy grouping on the phenyl is in the 4-position to the sulphonylurea group.

5. A substituted (quinolin-2-yl-methoxy)phenyl-N,N'-sulphonylurea or salt thereof according to claim 3, in which the quinolyl-methoxy group on the phenyl is in the 4-position to the sulphonylurea group, $R^1$ represents hydrogen, n-pentyl or cyclopentyl and $R^3$ represents benzyl.

6. A compound according to claim 1, wherein such compound is N-(4-methylphenylsulphonyl)-N'-cyclopentyl-N'-4-(2-quinolylmethoxy)-phenylurea of the formula

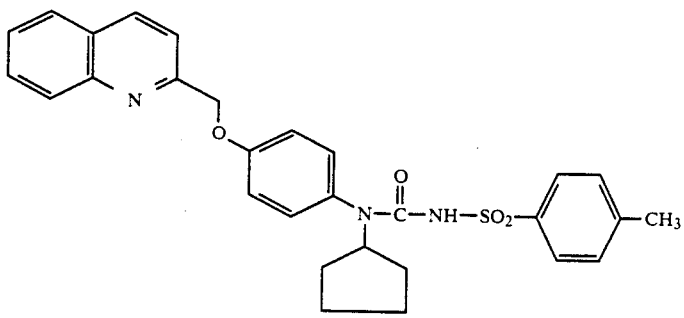

or a physiologically acceptable salt thereof.

7. A compound according to claim 1, wherein such compound is N-(2-methylphenylsulphonyl)-N'-cyclopentyl-N'-4-(2-quinolymethoxy)-phenylurea of the formula

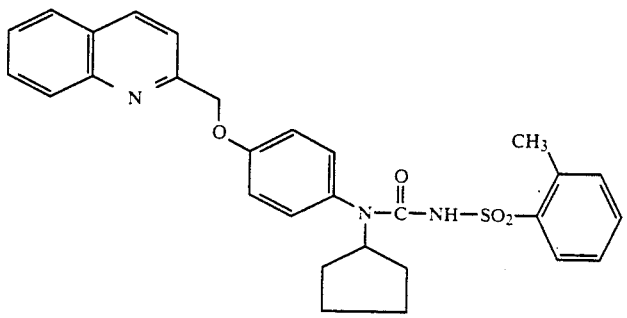

or a physiologically acceptable salt thereof.

8. A compound according to claim 1, wherein such compound is N-benzylsulphonyl-N'-4-(2-quinolinylmethoxy)-phenylurea of the formula

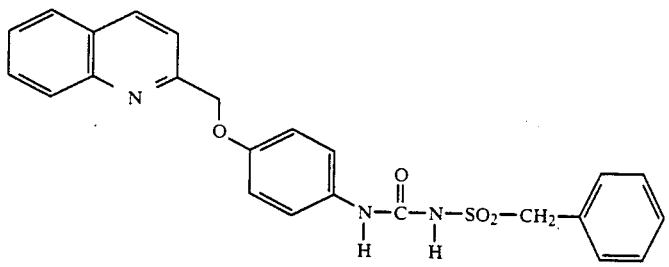

or a physiologically acceptable salt thereof.

9. A compound according to claim 1, wherein such compound is N-benzylsulphonyl-N'-n-pentyl-N'-4-(2-quinolinylmethoxy)-urea of the formula

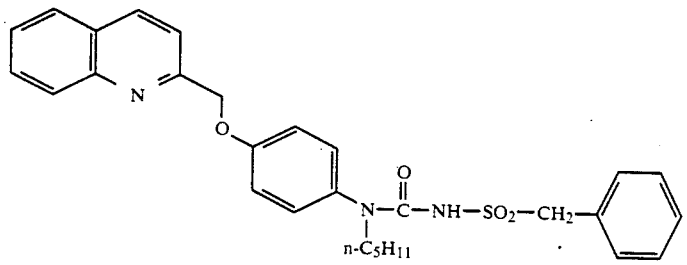

or a physiologically acceptable salt thereof.

10. A compound according to claim 1, wherein such compound is N-mesyl-N'-cyclohexyl-methyl-N'-4-(2-quinolinylmethoxy)-phenylurea of the formula

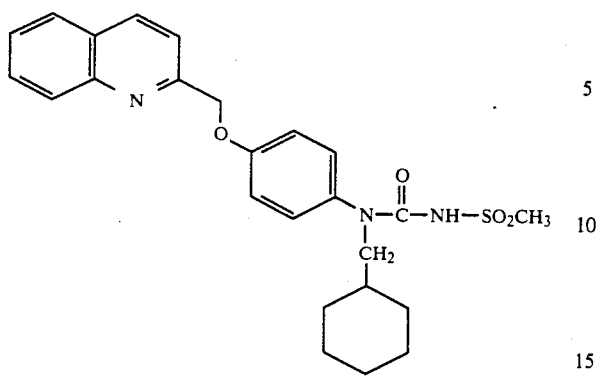

or a physiologically acceptable salt thereof.

11. A compound according to claim 1, wherein such compound is N-mesyl-N'-cyclopentyl-N'-4-(2-quinolinylmethoxy)-phenylurea of the formula

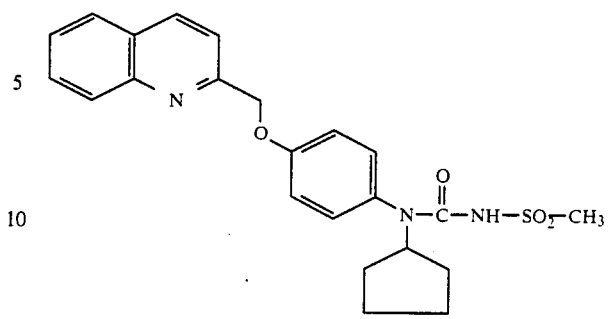

or a physiologically acceptable salt thereof.

12. A compound according to claim 1, wherein such compound is N-benzylsulphonyl-N'-cyclopentyl-N'-4-(2-quinolinyl-methoxy)-phenylurea of the formula

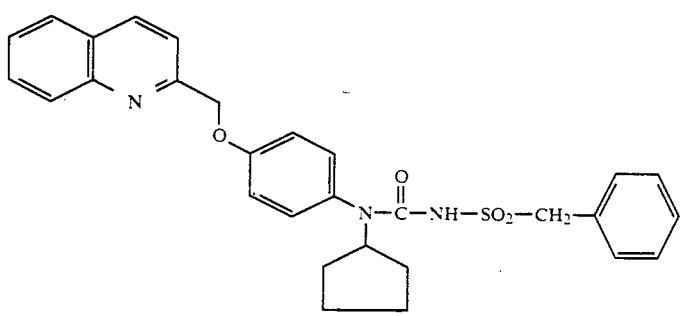

or a physiologically acceptable salt thereof.

13. A leukotriene-inhibiting composition comprising an amount effective therefor of a compound or salt thereof according to claim 1 and a physiologically acceptable diluent.

14. A method of inhibiting leukotriene in a patient in need thereof which comprises administering to such patient an amount effective therefor of a compound or salt thereof according to claim 1.

15. The method according to claim 14, wherein such compound is

N-(4-methylphenylsulphonyl)-N'-cyclopentyl-N'-4-(2-quinolylmethoxy)-phenylurea

N-(2-methylphenylsulphonyl)-N'- cyclopentyl-N'-4-(2-quinolylmethoxy)-phenylurea

N-benzylsulphonyl-N'-4-(2-quinolinylmethoxy)-phenylurea,

N-benzylsulphonyl-N'-n-pentyl-N'-4-(2-quinolinylmethoxy)-urea,

N-mesyl-N'-cyclohexyl-methyl-N'-4-(2-quinolinylmethoxy)-phenylurea,

N-mesyl-N'-cyclopentyl-N'-4-(2-quinolinylmethoxy)-phenylurea, or

N-benzylsulphonyl-N'-cyclopentyl-N'-4-(2-quinolinylmethoxy)-phenylurea, or a physiologically acceptable salt thereof.

* * * * *